United States Patent
Kim et al.

(10) Patent No.: US 10,696,612 B2
(45) Date of Patent: Jun. 30, 2020

(54) AMORPHOUS MOLECULAR MATERIAL AND SYNTHESIS METHOD THEREFOR

(71) Applicant: KOREA UNIVERSITY RESEARCH AND BUSINESS FOUNDATION, Seoul (KR)

(72) Inventors: Woong Kim, Seoul (KR); Ka Hoe Ku, Seoul (KR); Hee Yeon Park, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 126 days.

(21) Appl. No.: 15/765,118

(22) PCT Filed: Dec. 29, 2015

(86) PCT No.: PCT/KR2015/014432
§ 371 (c)(1),
(2) Date: Mar. 30, 2018

(87) PCT Pub. No.: WO2017/057802
PCT Pub. Date: Apr. 6, 2017

(65) Prior Publication Data
US 2018/0319725 A1    Nov. 8, 2018

(30) Foreign Application Priority Data

Sep. 30, 2015  (KR) .................. 10-2015-0137896

(51) Int. Cl.
| | | |
|---|---|---|
| C07C 15/16 | (2006.01) | |
| C09K 11/06 | (2006.01) | |
| C07C 15/52 | (2006.01) | |
| C07C 2/86 | (2006.01) | |
| C07C 1/20 | (2006.01) | |

(52) U.S. Cl.
CPC ............. *C07C 15/16* (2013.01); *C07C 1/20* (2013.01); *C07C 2/864* (2013.01); *C07C 15/52* (2013.01); *C09K 11/06* (2013.01); C07C 2527/054 (2013.01); C09K 2211/1007 (2013.01)

(58) Field of Classification Search
CPC ... C07C 15/16; C07C 1/20; C09K 2211/1007; C09K 11/06
USPC ......................... 585/24, 25, 26, 27
See application file for complete search history.

(56) References Cited

U.S. PATENT DOCUMENTS 3,387,050 A * 6/1968 Norell .................. C07C 5/367
                                                585/431
3,991,049 A * 11/1976 Siegrist .................. C07C 2/86
                                                546/350

(Continued)

FOREIGN PATENT DOCUMENTS

| KR | 10-2008-0028304 A | 3/2008 |
|----|---------------------|--------|
| WO | 02/20459 A1 | 3/2002 |

OTHER PUBLICATIONS

International Search Report for PCT/KR2015/014432 dated Jun. 21, 2016, citing the above references.

(Continued)

*Primary Examiner* — Ellen M McAvoy
(74) *Attorney, Agent, or Firm* — Hauptman Ham, LLP

(57) ABSTRACT

An amorphous molecular material having stilbene and benzyl group substituents at both side of stilbene has fluorescent characteristics.

1 Claim, 6 Drawing Sheets

(56) References Cited

U.S. PATENT DOCUMENTS

| | | | | |
|---|---|---|---|---|
| 4,859,556 A | * | 8/1989 | Sasaki | C07C 255/00 |
| | | | | 430/73 |
| 5,081,251 A | * | 1/1992 | Bender | C07C 13/48 |
| | | | | 546/350 |
| 6,617,051 B1 | * | 9/2003 | Higashi | C07C 13/48 |
| | | | | 210/767 |
| 8,664,263 B2 | | 3/2014 | Harue et al. | |
| 2007/0100180 A1 | * | 5/2007 | Egawa | C07C 15/60 |
| | | | | 585/26 |
| 2008/0081934 A1 | * | 4/2008 | Egawa | C07C 15/60 |
| | | | | 585/26 |
| 2008/0088229 A1 | | 4/2008 | Masakazu | |
| 2008/0091030 A1 | | 4/2008 | Masakazu et al. | |
| 2011/0140043 A1 | * | 6/2011 | Stoessel | C07D 209/86 |
| | | | | 252/301.16 |
| 2011/0204772 A1 | | 8/2011 | Masakazu | |
| 2012/0326042 A1 | * | 12/2012 | Zaitseva | C07C 15/14 |
| | | | | 250/361 R |

OTHER PUBLICATIONS

Korean Office Action issued in corresponding Korean Patent Application No. 10-2015-0137896 dated Apr. 24, 2017, citing the above references.

Bergmann et al., "Syntheses of Macrocyclic Compounds," Contribution from the Scientific Department, Israeli Ministry of Defence, vol. 75, Mar. 16, 1953, pp. 4281-4286.

Gault et al., "New diphenylmethane derivatives," Journal, Compt. rend., vol. 240, 1955, pp. 630-631.

Written Opinion for PCT/KR2015/014432 dated Jun. 21, 2016, citing the above references.

* cited by examiner

AMORPHOUS MOLECULAR MATERIAL AND SYNTHESIS METHOD THEREFOR

CROSS REFERENCE TO RELATED APPLICATION

This present application is a national stage filing under 35 U.S.C § 371 of PCT application number PCT/KR2015/014432 filed on Dec. 29, 2015 which is based upon and claims the benefit of priority to Korean Patent Application No. 10-2015-0137896 filed on Sep. 30, 2015 in the Korean Intellectual Property Office. The disclosures of the above-listed applications are hereby incorporated by reference herein in their entirety.

TECHNICAL FIELD

The present invention relates to an amorphous molecular material and a method of synthesizing the same. More particularly, the present invention relates to an amorphous molecular material having improved fluorescent characteristics and being capable of being more easily synthesized, compared with the conventional amorphous molecular materials.

BACKGROUND ART

Fluorescent amorphous carbon molecules may have high purities and monodispere properties, compared with a polymer material. The fluorescent amorphous carbon molecules may have optically transparent properties and fluorescent properties capable of emitting light. Thus, the fluorescent amorphous carbon molecules may be optically used for various fields.

Various researches about several methods or processes for synthesizing the fluorescent amorphous carbon molecules have been performed for the long time, However, the conventional researches have revealed relatively complex processes for synthesizing the fluorescent amorphous carbon molecules. That is, according to the conventional methods of synthesizing the fluorescent amorphous carbon molecule, there are lots of issues, which should be required to be solved, such as a total synthesis time, a synthesis efficiency, an economic matter, etc. In order to solve these issues, research and development about economical and efficient methods for synthesizing the fluorescent amorphous carbon molecules are required. Furthermore, a wide application of the fluorescent amorphous carbon molecules can be further available through the application of various molding methods or patterning methods such as a nano imprinting process for forming a pattern on a glass material.

DETAILED DESCRIPTION OF THE INVENTION

Technical Problem

A purpose of the present invention is to provide an amorphous molecular material having an improved fluorescent property.

Another purpose of the present invention is to provide a method of easily synthesizing an amorphous molecular material having an improved fluorescent property.

Technical Solution

In order to achieve the above-mentioned purpose of the present invention, an amorphous molecular material in accordance with example embodiments of the present invention includes stilbene and benzyl group substituents bonded on both sides of stilbene.

In an example embodiment, the stilbene may include a cis-isomer and a trans-isomer. When the stilbene is the cis-isomer, the stilbene having a fluorescent characteristic may represent formula 1:

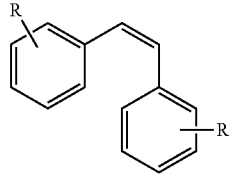

Formula 1

Here, R is benzyl group.

In an example embodiment, when the stilbene is the tran-isomer, the stilbene having a fluorescent characteristic may represent formula 2;

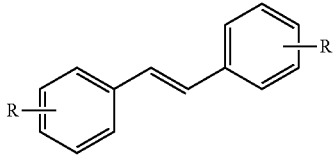

Formula 2

Here, R is benzyl group.

In an example embodiment, the amorphous molecular material may include positional isomers according to a bonding position of the benzyl group substituents.

In an example embodiment, wherein the amorphous molecular material may have a maximum fluorescent property when light having a wavelength of 420 is irradiated.

In an example embodiment, the amorphous molecular material may have a refractive index of 1.66 to 1.71 in a visible light vision.

In an example embodiment, the amorphous molecular material may have a glass transition temperature of about 30° C.

According to a method of synthesizing an amorphous molecular material in accordance with example embodiments of the present invention, an aqueous sulfuric acid solution is added to a benzyl alcohol precursor to form a mixture. And then, a heatup process is performed against the mixture to form an amorphous material being composed of stilbene and a benzyl group substituents bonded on both sides of stilbene.

In an example embodiment, the heatup process against the mixture is performed at a temperature of 150 to 200° C. and for a process time of 5 to 24 hours.

Advantageous Effects

According to embodiments of the present invention, the amorphous molecular material has improved fluorescence property as the amorphous molecular material has improved fluorescence property has a quantum yield in the range of 61 to 73%. Also, the amorphous molecular material has a relatively high refractive index when the visible light region is applied. In addition, the amorphous molecular material can be easily treated at a relatively low temperature as the amorphous molecular material has a glass transition temperature of about 30° C. As a result, the amorphous molecular material can be molded through a molding process, a blowing process, or a nano imprinting process.

BEST MODE OF THE INVENTION

Figure 1A:
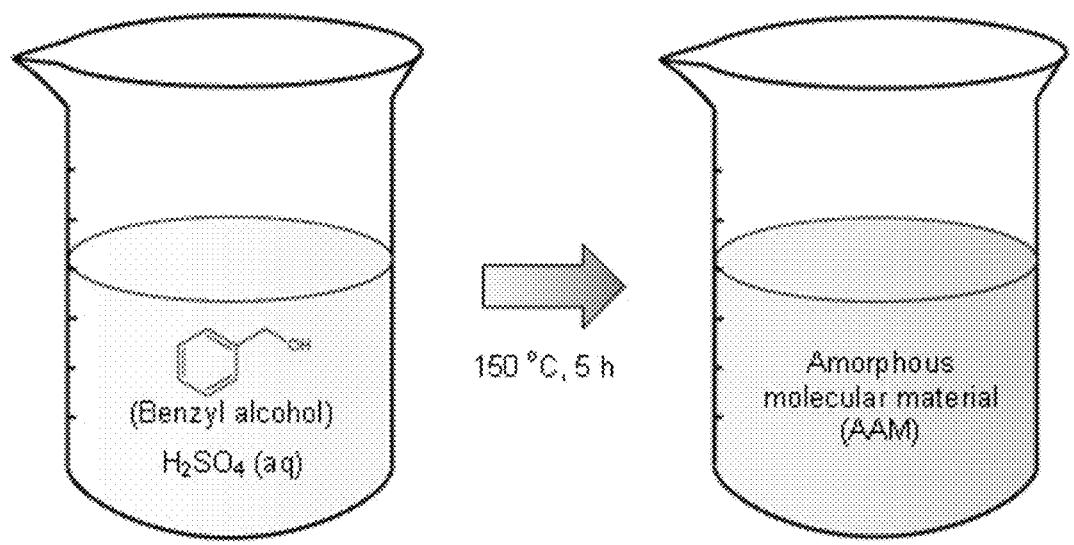
FIGS. 1A, 1B, 1C, 1D and 1E depict a method of synthesizing amorphous molecule materials and amorphous molecular materials synthesized by the method in accordance with example embodiments of the present invention.

Various example embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this disclosure will be thorough and complete, and will fully convey the scope of the present inventive concept to those skilled in the art. In the drawings, the sizes and relative sizes of layers and regions may be exaggerated for clarity. Like numerals refer to like elements throughout.

It will be understood that, although the terms first, second, etc. may be used herein to describe various elements, these elements should not be limited by these terms. These terms are used to distinguish one element from another. For example, a first element discussed below could be termed a second element without departing from the teachings of the present inventive concept. Also, a second element discussed below could be termed a first element without departing from the teachings of the present inventive concept. As used herein, the singular forms are intended to include the plural forms as well, unless the context clearly indicates otherwise.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.). It will be understood that, although the terms first, second, third etc. may be used herein to describe various elements, these elements should not be limited by these terms. These terms are used to distinguish one element from another. Thus, a first element discussed below could be termed a second element without departing from the teachings of the present inventive concept. As used herein, the term "and/or" includes any and all combinations of one or more of the associated listed items.

Meanwhile, the terminology used herein is for the purpose of describing particular example embodiments only and is not intended to be limiting of the present inventive concept. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

An amorphous molecular material in accordance with example embodiments of the present invention includes stilbene and benzyl group substituents bonded on both sides of stilbene.

The stilbene may include a cis-isomer and a trans-isomer. When the stilbene is the cis-isomer, the stilbene having a fluorescent characteristic may represent formula 1;

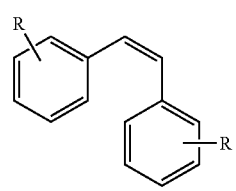

Formula 1

Here, R is benzyl group.

When the stilbene is the tran-isomer, the stilbene having a fluorescent characteristic may represent formula 2;

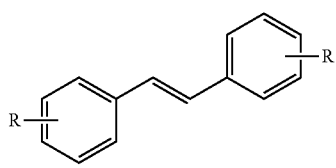

Formula 2

Here, R is benzyl group.

Modes of the Inventions

Amorphous Molecular Material

An amorphous molecular material in accordance with example embodiments of the present invention includes stilbene and benzyl group substituents bonded on both sides of stilbene.

The stilbene may include a cis-isomer and a trans-isomer. When the stilbene is the cis-isomer, the stilbene having a fluorescent characteristic may represent formula 1;

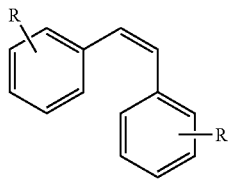

Formula 1

Here, R is benzyl group.

When the stilbene is the tran-isomer, the stilbene having a fluorescent characteristic may represent formula 2;

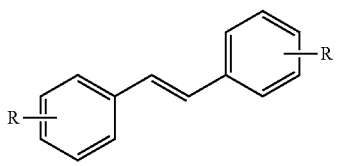

Formula 2

Here, R is benzyl group.

Further, the amorphous molecular material may have positional isomers according to a bonding position of R in the structural formula (1). That is, an ortho, meta or para-isomer may exist in accordance with each of the bonding position at which R is bonded to each of benzene rings positioned at both ends.

The amorphous molecular material may have a maximum fluorescence property when light having a wavelength of 420 nm is irradiated. That is, when the amorphous molecular material is exposed to ultraviolet light, the amorphous molecular material may emit a blue fluorescent color.

On the other hand, the amorphous molecular material may have a refractive index of 1.66 to 1.71 with respect to a visible light region. That is, the amorphous molecular material has a higher refractive index than a general carbon-based material. As a result, the amorphous molecular material may be utilized for forming a photo-coating tube.

In addition, the amorphous molecular material has a glass transition temperature close to 30° C. Thus, the amorphous molecular material may be utilized for performing a molding process at a relatively low temperature, therefore to be easily patterned in a low-temperature process.

Method of Synthesizing Amorphous Molecular Material

FIGS. 1A, 1B, 1C, 1D and 1E depict a method of synthesizing amorphous molecule materials and amorphous molecular materials synthesized by the method in accordance with example embodiments of the present invention.

Referring to FIG. 1A, an aqueous sulfuric acid solution is added to a benzyl alcohol precursor to form a mixture. An example of the benzyl alcohol precursor is benzyl alcohol. Alternatively, the benzyl alcohol precursor may include alcohol-based benzene derivatives such as phenethyl alcohol, 3-phenyl-1-propanol and 2-phenylpropanol, and alcohol-based polyacene derivatives such as naphthyl alcohol and anthryl alcohol.

The sulfuric acid aqueous solution added to the benzyl alcohol precursor may include dilute sulfuric acid aqueous solution, which is mixed with sulfuric acid and pure water at a volume ratio of 1:3.

Subsequently, the heat-up process is performed against the mixture to obtain amorphous molecular material from the mixture. When the amorphous molecular material is obtained through the heat-up process, the heat-up process can have a considerably high yield in a range of about 80 to 88%.

As a result, the amorphous molecular material having a fluorescent characteristic includes stilbene and benzyl group substituents bonded on both sides of stilbene.

The stilbene may include a cis-isomer and a trans-isomer. When the stilbene is the cis-isomer, the stilbene having a fluorescent characteristic may represent formula 1;

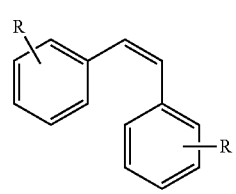

Formula 1

Here, R is benzyl group.

When the stilbene is the tran-isomer, the stilbene having a fluorescent characteristic may represent formula 2;

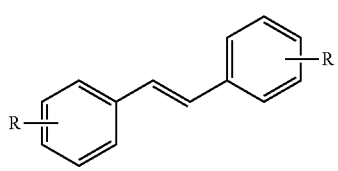

Formula 2

Here, R is benzyl group.

Further, the amorphous molecular material may have position isomers depending on the bonding position of R in the structural formula (1). That is, an ortho, meta or para-isomer may be formed depending on the bonding position at which R is bonded to each of benzene rings positioned at both ends.

The heat-up process against the mixture may be carried out at a temperature of 150 to 200° C. for 5 to 24 hours. The above temperature and process time are shown in Table 1 as below;

TABLE 1

| Process temperature (° C.) | Process Time (hour) | Quantum efficiency (%) |
| --- | --- | --- |
| 120 | 5 | N/A |
| 150 | 0.5 | N/A |
|  | 2 | N/A |
|  | 5 | 61 |
|  | 24 | 73 |
| 165 | 5 | 47 |
| 180 | 5 | 47 |
| 200 | 5 | 36 |

Benzyl alcohol precursor (15 ml) was mixed with a dilute sulfuric acid aqueous solution (1 ml) including sulfuric acid and pure water at a volume ratio of 1:3 to form a mixture. Thereafter, the mixture was subjected to a heat-up process at a temperature of 150° C. for 5 hours. As a result, an amorphous molecular material was synthesized. Properties of the amorphous molecular material were tested.

Figure 1B:
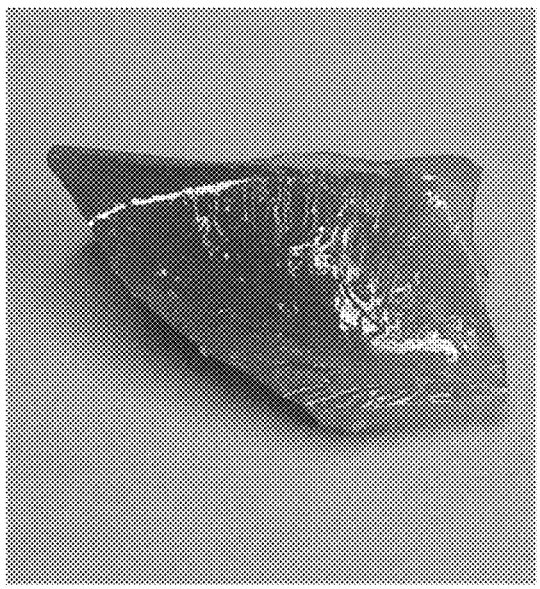

Referring to FIG. 1B, amorphous molecular material in a bulk state is shown. The amorphous molecular material has the conchoidal fracture of the crystal. Thus, it could be known that the amorphous molecular material has an amorphous property.

Figure 1C:
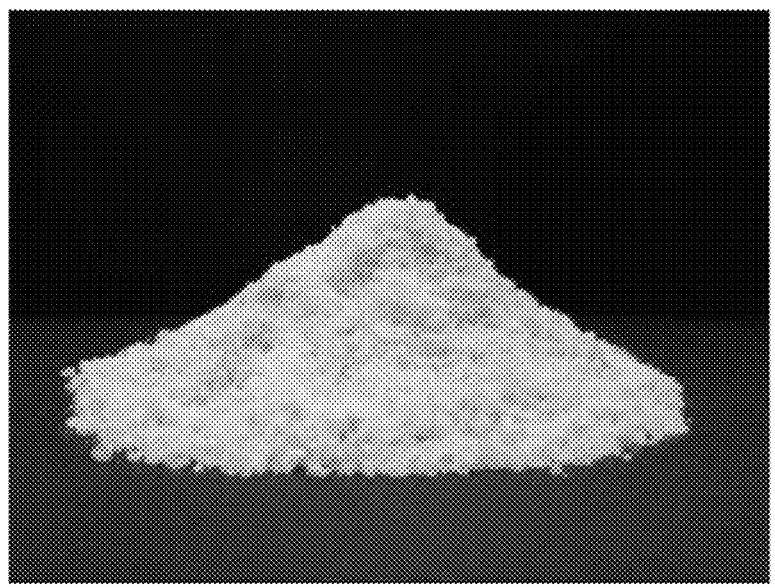
Figure 1D:

Referring to FIGS. 1C & 1D, it could be kwon that the amorphous molecular material having a powder state exhibits blue fluorescence when exposed to ultraviolet light.

Figure 1E:
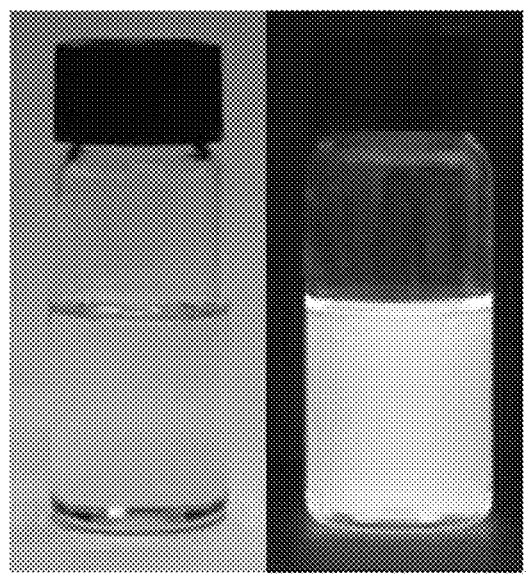

Referring to FIG. 1E, when the amorphous molecular material is dispersed in a toluene solution. it can be acknowledged that the amorphous molecular material is uniformly dispersed in the toluene solution to exhibit blue-based fluorescence characteristics as a whole.

Evaluation of Amorphous Molecular Material

Figure 2:
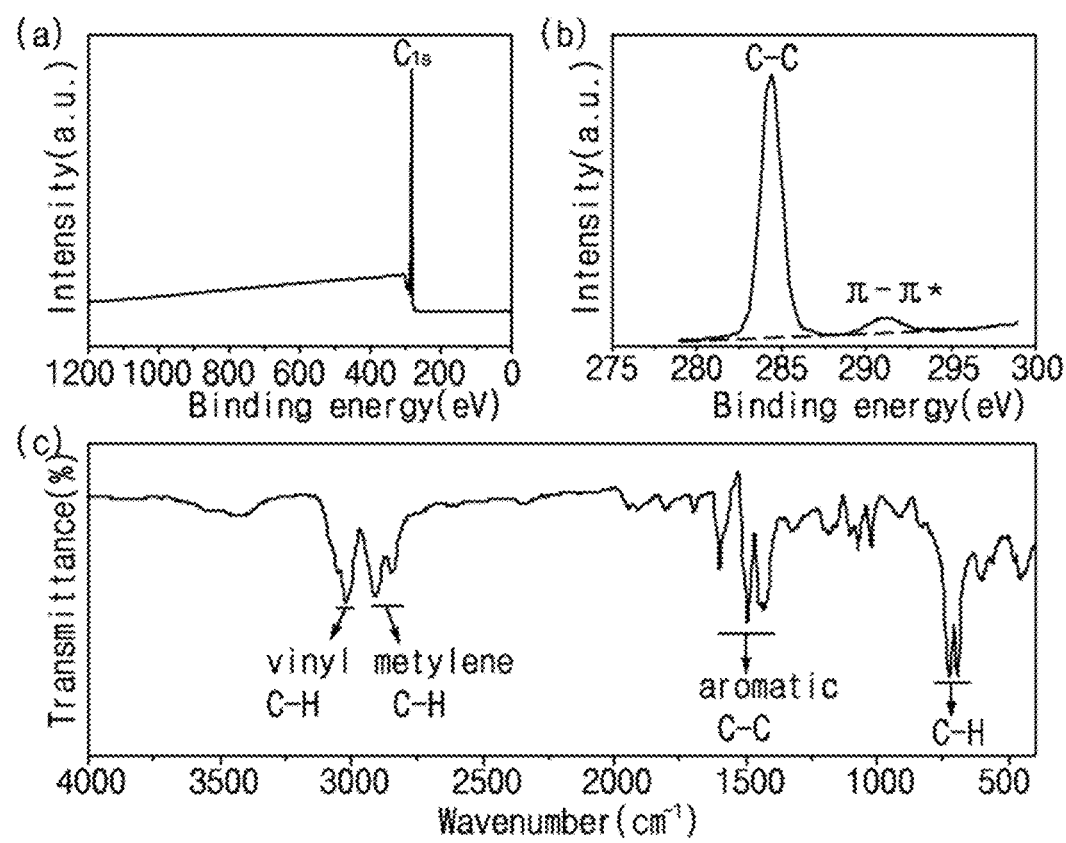
FIG. 2 is a plurality of graphs for analyzing a molecular structure of amorphous molecular material in accordance with example embodiments of the present invention.

FIG. 2 is a plurality of graphs for analyzing a molecular structure of amorphous molecular materials in accordance with example embodiments of the present invention.

Referring to FIG. 2 (a), a X-ray spectroscopy (XPS) analyses elemental content ratios of amorphous molecular material. Here, it can be acknowledge that oxygen and sulfuric acid are not contained in the amorphous molecular material.

Referring to FIG. 2 (b), C1s XPS analysis method is performed to analyze a carbon bond structure of the amorphous molecular material. Here, it may be predictable that the amorphous molecular material has an aromatic structure by detecting the C—C bonding peak and the π-π shake-up satellite peak.

Referring to FIG. 2 (c), a type of bonding structure of the amorphous molecular material is acknowledged through an FT-IR analysis. It can be known that a structure of the amorphous molecular material is a methylene and aromatic structure.

Figure 3:
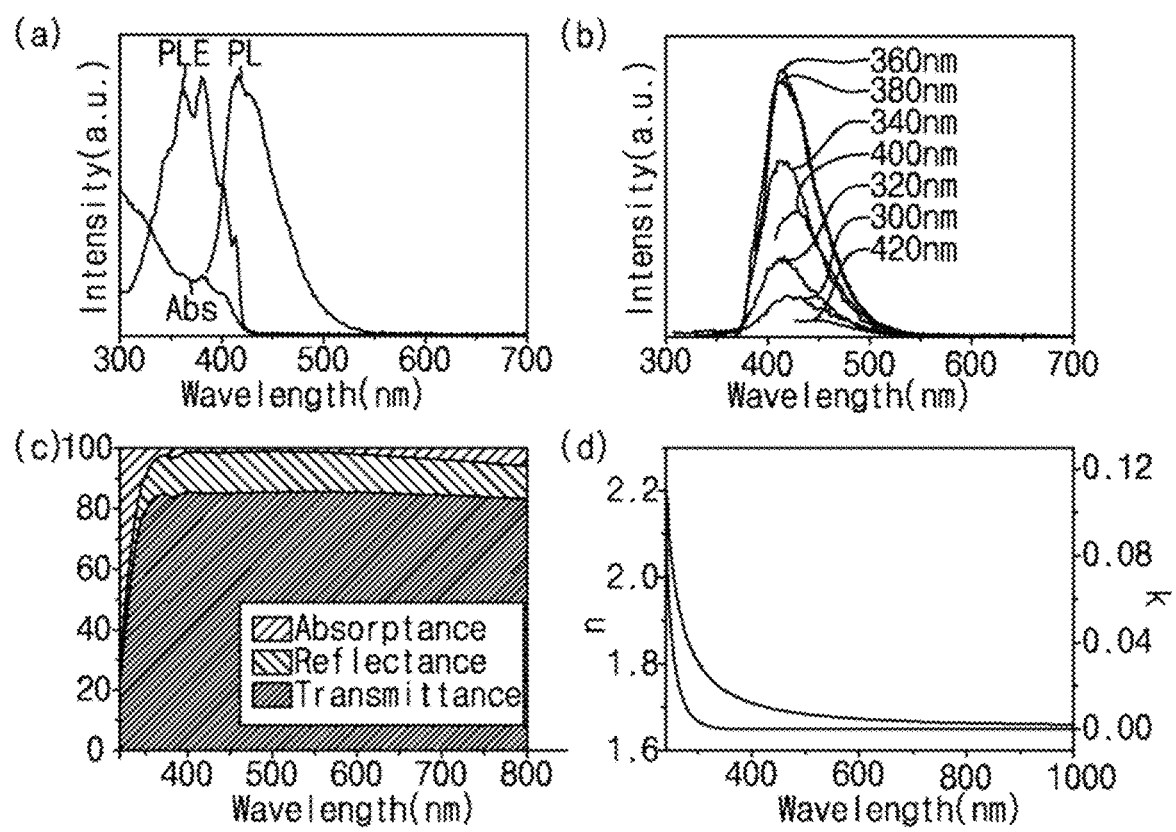
FIG. 3 is a plurality of graphs for analyzing an optical property of amorphous molecular material in accordance with example embodiments of the present invention.

FIG. 3 is a plurality of graphs for analyzing an optical property of amorphous molecular materials in accordance with example embodiments of the present invention.

Referring to FIG. 3 (a), absorbance, photoluminescence, and photoluminescence excitation characteristics of the amorphous molecular material solution are measured. The amorphous molecular materials have remarkably high absorption against light in a range of the ultraviolet light region. On the other hands, it could not be observed that the amorphous molecular materials have an absorption against the visible light. Further, the fluorescence property is found to be maximum in the blue fluorescent region corresponding to a wavelength of 420 nm.

Referring to FIG. 3 (b), data on photoluminescence for various excitation wavelengths are obtained. It could be seen from the graph that there is no unusually large PL-shift phenomenon.

Referring to FIG. 3 (c), an amorphous molecular material thin film is examined in order to check an absorptance, a reflectance, and a transmittance of light. It is found that the thin film has a high transmittance over the entire visible light region.

Referring to FIG. 3 (d), an analysis of ellipsometry characteristics is analyzed against the amorphous molecular material thin film. The amorphous molecular material thin film has a refractive index in the visible light region in a range of 1.66 to 1.71, which means that The amorphous molecular material has a considerably high refractive index as a carbon-based material.

On the other hand, the extinction coefficient shows a value of "0" with respect to the visible light region, which indicates that it exhibits excellent transmittance to visible light.

Figure 4:
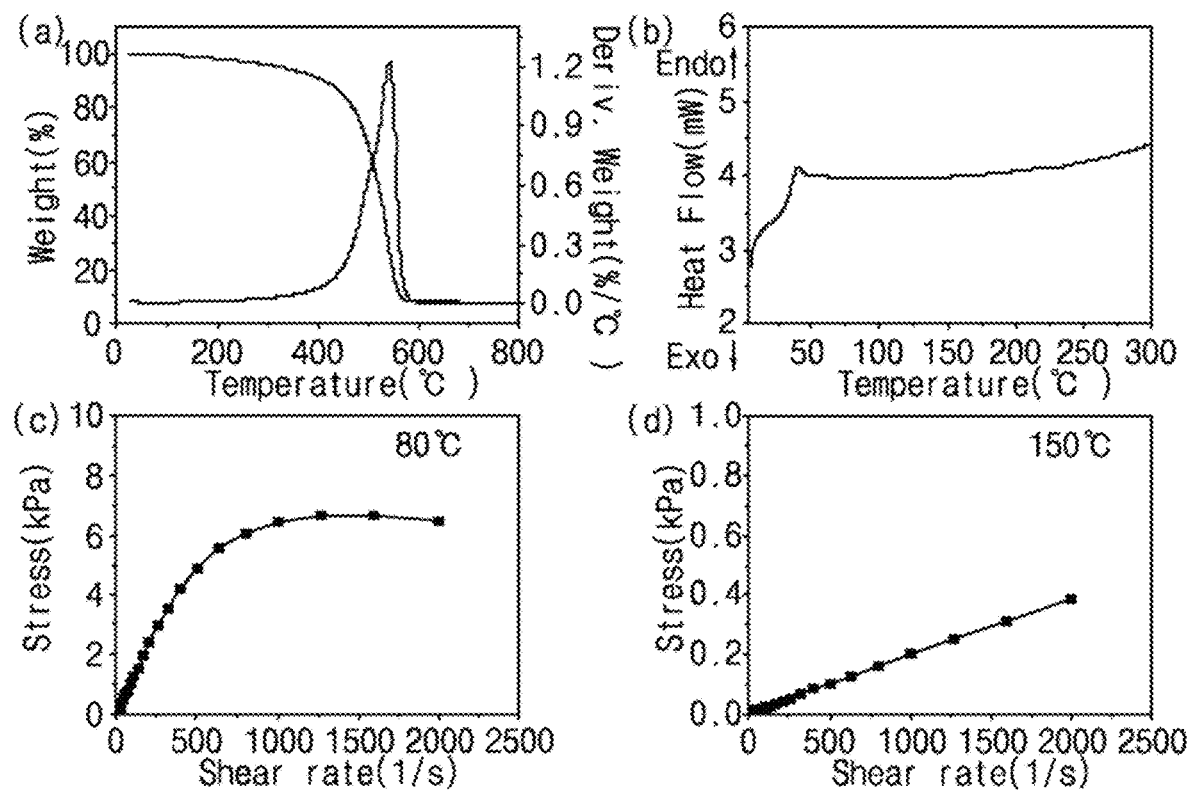
FIG. 4 is a plurality of graphs for analyzing thermal/rheological properties of amorphous molecular material in accordance with example embodiments of the present invention.

FIG. 4 is a plurality of graphs for analyzing thermal/rheological properties of amorphous molecular materials in accordance with example embodiments of the present invention.

Referring to FIG. 4 (a), a thermogravimetric analysis (TGA) and a derivative thermogravimetric analysis (DTG) were performed against the amorphous molecular material. It is found that the approximate decomposition temperature is over 400° C.

Referring to FIG. 4 (b), a differential scanning calorimetric (DSC) analysis is perpformed against the amorphous molecular material such that a glass transition temperature of the amorphous molecular material is found to be about 30° C. Therefore, it means that the amorphous molecular material exhibits a glassy behavior, and it has a relatively low glass transition temperature, which means that a behavior of the amorphous molecular material may be sufficiently changed at a relatively low temperature.

Referring to FIG. 4 (c), rheological characteristics of the amorphous molecular material at 80° C. indicate that a viscosity decreases as a shear rate increases, which means that the amorphous molecular material shows a shear thinning behavior such as pseudo plastic fluid. This implies that it is possible to apply the amorphous molecular material to a polymeric or a glassy process in the above-mentioned processing temperature range.

Referring to FIG. 4 (d), the rheological characteristics analysis are performed against the amorphous molecular material at 150° C. such that the amorphous molecular material shows a behavior of the Newtonian fluid having a constant viscosity irrespective of changes in the shear rate.

Figure 5A:
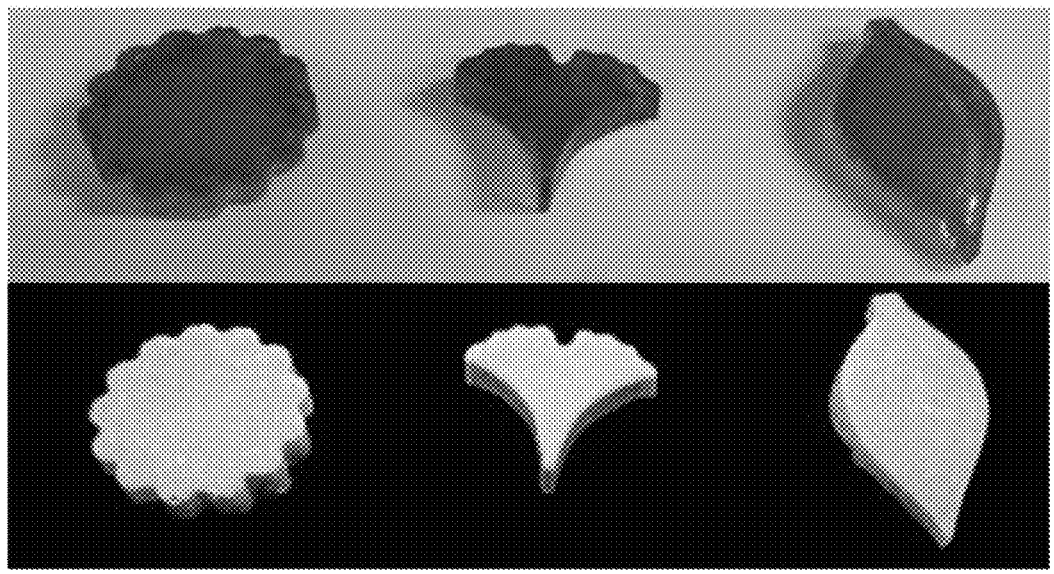
FIGS. 5A, 5B and 5C are photographs showing molded products which are formed using amorphous molecular materials in accordance with an example embodiment of the present invention.
Figure 5B:
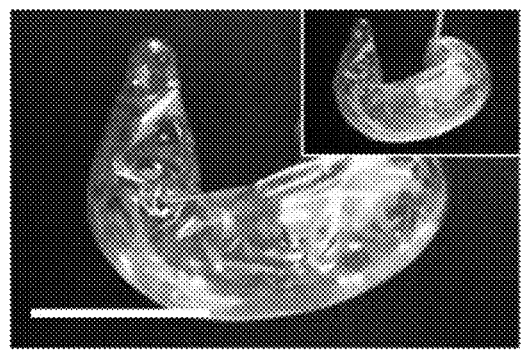
Figure 5C:
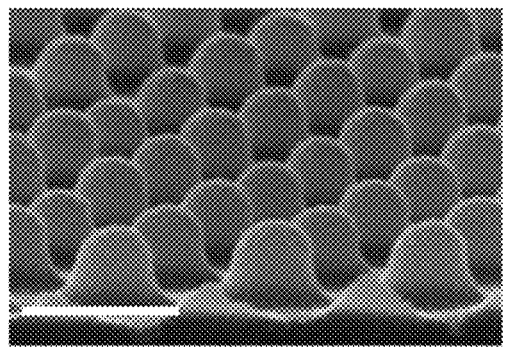

FIGS. 5A, 5B and 5C are photographs showing molded products that are formed using amorphous molecular materials in accordance with an example embodiment of the present invention.

Referring to FIG. 5A, an image of a mass of an amorphous molecular bulk formed in a specific form through a silicone mold is shown. The amorphous molecular bulk exhibits blue fluorescence when exposed to ultraviolet (UV).

Referring to FIG. 5 B, an image of of an amorphous molecular balloon having the same shape as a balloon, which are formed through the blowing process is shown. It can be know that it has optical properties of transparency and fluorescence as well.

FIG. 5C is a scanning electron microscope (SEM) image of an amorphous molecular material having nano patterns, which are formed through an imprinting process.

Figure 6:
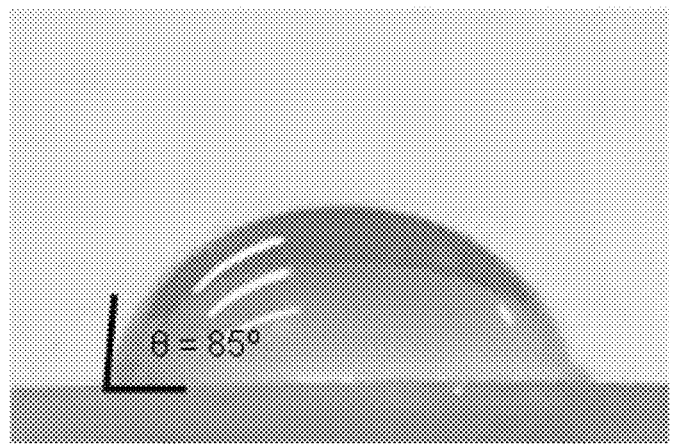
FIG. 6 is a photograph illustrating a contact angle of amorphous molecular materials in accordance with an example embodiment of the present invention.

FIG. 6 is a photograph illustrating a contact angle of amorphous molecular materials in accordance with an example embodiment of the present invention.

Referring to FIG. 6, the amorphous molecular material has a contact angle of 85°, which means that the amorphous molecular material has a hydrophobic property.

The amorphous molecular material according to example embodiments of the present invention can be applied to an ultraviolet protective film, an optical waveguide, a fluorescent diode, a photonic crystal, a super hydrophobic device, an optical lens, a reflector, and the like.

The foregoing is illustrative of the present teachings and is not to be construed as limiting thereof. Although a few exemplary embodiments have been described, those skilled in the art will readily appreciate from the foregoing that many modifications are possible in the exemplary embodiments without materially departing from the novel teachings and advantages of the present disclosure of invention. Accordingly, all such modifications are intended to be included within the scope of the present teachings. In the claims, means-plus-function clauses are intended to cover the structures described herein as performing the recited function and not only structural equivalents but also functionally equivalent structures.

The invention claimed is:

1. A method of synthesizing an amorphous molecular material, comprising:
   adding an aqueous sulfuric acid solution to a benzyl alcohol precursor to form a mixture; and
   performing a heating process against the mixture to form an amorphous material being composed of stilbene and a benzyl group substituents bonded on both sides of stilbene,
   wherein the heating processs against the mixture is performed at a temperature of 150 to 200° C. and for a process time of 5 to 24 hours.

* * * * *